United States Patent [19]
Girijavallabhan et al.
[11] Patent Number: 4,584,133
[45] Date of Patent: Apr. 22, 1986

[54] PROCESS FOR THE PRODUCTION OF PENEMS

[75] Inventors: Viyyoor M. Girijavallabhan, Parsippany; Ashit K. Ganguly, Upper Montclair; Patrick A. Pinto, Mine Hill; Richard W. Versace, Ringwood, all of N.J.

[73] Assignee: Schering Corporation, Kenilworth, N.J.

[21] Appl. No.: 549,535

[22] Filed: Nov. 7, 1983

[51] Int. Cl.[4] .................... C07D 205/08; C07D 487/04
[52] U.S. Cl. .......................... 260/245.2 R; 260/239 A
[58] Field of Search .................................. 260/245.2 R

[56] References Cited

U.S. PATENT DOCUMENTS 4,443,373 4/1984 Girijavallabhan ........... 260/245.2 R

OTHER PUBLICATIONS

Fieser, "Advanced Organic Chemistry", pp. 310-320, (1965).
Fieser, "Organic Chemistry", 3rd Edition, pp. 325, 329, 337-342, (1958).
Gould, "Mechanism and Structure in Organic Chemistry", pp. 258-262, 276-279, (1959).
March, "Advanced Organic Chemistry", pp. 251-263, (1968).
Morrison, "Organic Chemistry", 2nd Edition, pp. 661-666, (1966).

*Primary Examiner*—Mark L. Berch
*Attorney, Agent, or Firm*—Gerald S. Rosen; Anita W. Magatti

[57] ABSTRACT

Improved processes for the production of 6-hydroxyethyl-2-substituted thio penem-3-carboxylates which eliminate the step of using a silver reagent are disclosed.

1 Claim, No Drawings

PROCESS FOR THE PRODUCTION OF PENEMS

BACKGROUND

This invention relates to an improved process for preparing 6-hydroxyethyl-2-substituted thio-penem-3-carboxylates (referred to herein as penems). Penems are a recent addition to the family of synthetic beta-lactams and possess potent antibacterial activity.

Multistep processes for producing penems using a silver containing intermediate are disclosed in U.S. Pat. No. 4,443,393 and in our copending U.S. patent application Ser. No. 445,295, filed Nov. 29, 1982, now U.S. Pat. No. 4,530,793. These processes result in high yields, however, they are not economical since they require the use of an expensive silver containing reagent.

The process of this invention eliminates the need for the silver containing reagent while still resulting in high yields. Furthermore, in the process of this invention the compounds produced are essentially one isomeric form which results from the particular isomeric form of the azetidinone intermediate.

SUMMARY OF THE INVENTION

The present invention provides a novel, facile process which is widely applicable for preparing 2-substituted thio penems and which is more economical than previous penem producing processes and employs fewer steps and reagents.

The process of this invention eliminates the need for process step (d) in U.S. Pat. No. 4,443,373 and process step (d) of processes A and B and process step (b) of process C in Ser. No. 445,295, filed November 29, 1982, now U.S. Pat. No. 4,530,793. The process of this invention is suitable for preparing penems represented by the formula:

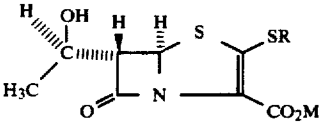

I wherein R is a pharmaceutically acceptable organic radical and M is hydrogen or an alkali metal cation.

The processes improved upon by this invention are multistep processes. The improvement of this invention is the elimination of process steps while maintaining the ease of conducting the process and the high yields. The economics of the processes are improved significantly by this invention.

The improved process step is the treatment of the following intermediate

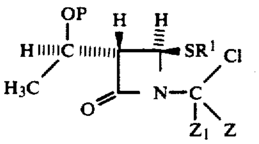

V with a stoichiometric excess elemental zinc in hydrochloric acid or other strong acid to effect removal of the chlorine, $R^1$ and the removable hydroxy protecting group, P, if present, to yield a compound of the following formula

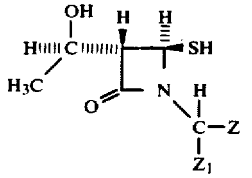

VI wherein P is a removable hydroxy protecting group or hydrogen; $R^1$ is a sulfur protecting group selected from triphenylmethyl(trityl), diphenylmethyl, 2-pyranyl, or lower alkyl carbonyl;

Z and $Z_1$ independently are $-COOCH_2CH_2R_2$ or $-COOCH_2CH=CH_2$;

$R_2$ is trimethylsilyl, t-butyldiphenylsilyl or other equivalently functioning lower alkyl silyl groups, cyano or a sulfone of the formula $-SO_2$-aryl.

Compound VI is then cyclized to a thione by reaction with a thiocarbonyl reagent.

This invention in another aspect relates to the preparation of a tautomeric thione of the following formulas

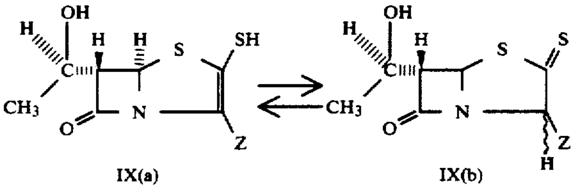

IX(a) IX(b)

wherein Z is as defined above.

Compounds of formula IX(a) and IX(b) are intermediates useful for the facile synthesis of penems as described hereinafter.

DETAILED DESCRIPTION OF THE INVENTION

The present invention provides a process hereinafter referred to as process A, for the production of penems of the formula:

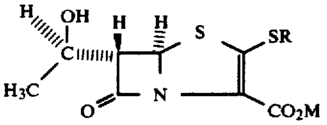

I wherein R is an organic radical and M is hydrogen or an alkali metal cation; which comprises (a) reaction of an azetidinone of the formula

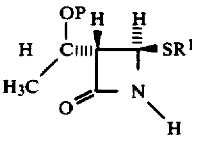

II wherein P is a removable hydroxy protecting group or hydrogen; and $R^1$ is a sulfur protecting group selected from triphenylmethyl, diphenylmethyl, 2-pyranyl, or lower alkyl carbonyl; with a compound of the formula IIIa and IIIb.

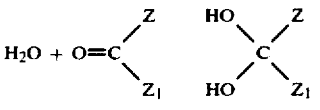

IIIa IIIb wherein Z and $Z_1$ are independently $—COOCH_2CH_2R_2$ or $—COOCH_2CH{=}CH_2$; $R_2$ is trimethylsilyl, t-butyldiphenylsilyl or other equivalently functioning lower alkylsilyl groups, cyano or a sulfone of the formula $—SO_2$-aryl; to form the intermediate of the formula IV

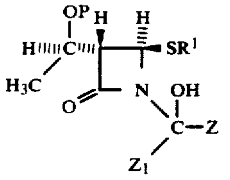

wherein P, $R^1$, Z and $Z_1$ are as hereinabove defined;

(b) treatment of the compound of formula IV with a chlorinating agent to form the following compound of formula V

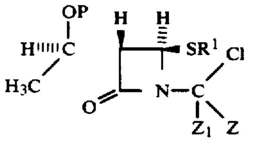

V wherein P, $R^1$, Z and $Z_1$ are as defined hereinabove;

(c) treatment of the compound of formula V with a stoichiometric excess of elemental zinc in a strong acid such as hydrochloric acid to effect removal of the chlorine and the removable sulfur and hydroxy protecting groups, and, if a removable hydroxy protecting group is utilized which is not removable with zinc, subsequent removal of said hydroxy protecting group, producing a compound of formula VI

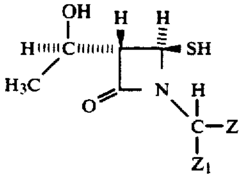

VI wherein Z and $Z_1$ are as hereinabove defined;

(d) treatment of the compound of formula VI with a hydroxy protecting group to form the compound of formula VI(a)

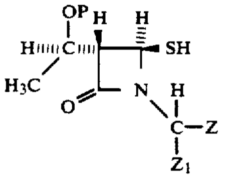

VI(a)

wherein Z and $Z_1$ are defined hereinabove and P is a hydroxy protecting group as defined hereinabove;

(e) reaction of the compound of formula VI or VI(a) with a thiocarbonyl compound of formula VII $$S{=}C(—Y)_2 \qquad VII$$

wherein Y is a leaving group; to form a compound of formula VIII

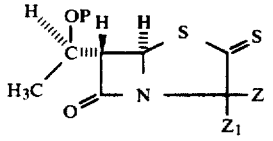

VIII wherein P, Z and $Z_1$ are as hereinabove defined;

(f) treatment of the compound of formula VIII wherein P is a hydroxy protecting group with an aqueous acid solution to deprotect the hydroxy group to form a compound of formula VIII(a)

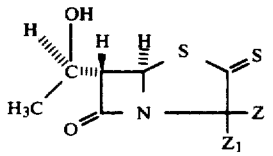

VIII(a)

wherein Z and $Z_1$ are as hereinabove defined;

In an alternative procedure, compounds of formula VIII(a) can be prepared from compounds of formula V by eliminating steps (d) and (f) (i.e., the protection and subsequent deprotection of the hydroxyl group at the C-8 position).

(g) treatment of the compound of formula VIII(a) with a fluoride ion (when Z is $—COOCH_2CH_2R_2$ only one equivalent of fluoride is used) to form the compound of formula IX(a) which is tautomeric with formula IX(b)

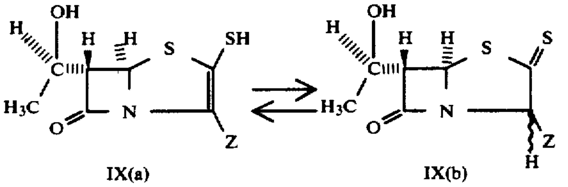

IX(a) IX(b)

wherein Z is as defined above.

(h) reaction of the tautomer of formulas IX(a) and IX(b) with either a compound of the formula X $$R—Z^2 \qquad X$$

wherein R is as defined hereinabove and $Z^2$ is a leaving group or with

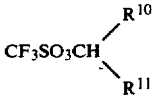

wherein $R^{10}$ is hydrogen or trifluoro lower alkyl and $R^{11}$ is trifluoroloweralkyl or dihydroxyloweralkyl or with $R_3$—CH═$CH_2$ wherein $R_3$ is hydrogen or methyl to form a compound of formula XI

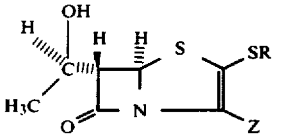

XI wherein R and Z are as defined above.

(i) treatment of a compound of formula XI under catalytic conditions when Z is —$COOCH_2CH$═$CH_2$ to remove the allyl protecting group in the presence of an alkali base (if the product is a zwittzerion, deprotection requires only the catalyst and any mild nucleophile, e.g. $H_2O$, alcohol, etc.) or if Z is —$COOCH_2CH_2R_2$ treating the compound of formula XI with one equivalent of fluoride ion to form the compounds of formula I

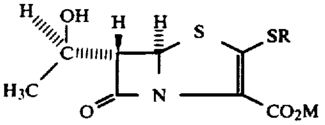

I wherein R and M are as hereinabove defined.

The process hereinafter referred to as process B, according to this invention is the preparation of a compound of the formulas IX(a) and IX(b)

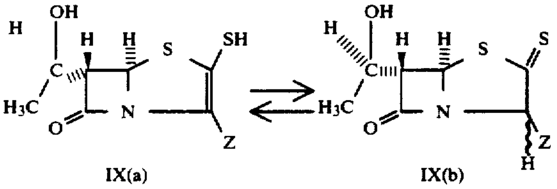

IX(a) IX(b)

and comprises steps (a) to (g) of Process A, above.

The preferred process of this invention, hereinafter referred to as Process C, is for preparing the following preferred intermediate compound of formulas IX(a) and IX(b)

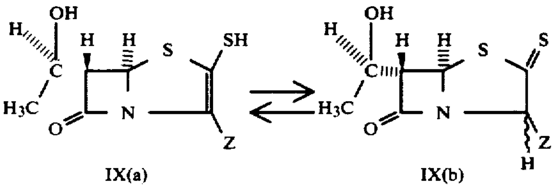

IX(a) IX(b)

and comprises the steps of (a) reaction of the azetidinone of formula II in which P is hydrogen as in the following formula II(a)

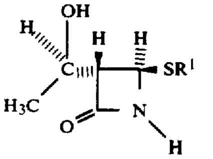

II(a)

wherein $R^1$ is a sulfur protecting group selected from triphenylmethyl, diphenylmethyl, 2-pyranyl, or lower alkyl carbonyl; with an allyl α-substituted acetate of formula XII $$WCH_2\overset{\overset{O}{\|}}{C}OCH_2CH{=}CH_2 \qquad XII$$

wherein W is a leaving group; to form the intermediate of the formula XIII

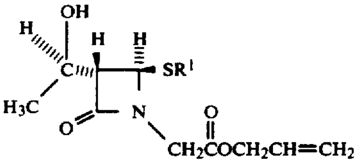

XIII wherein $R^1$ is as defined hereinabove;

(b) treatment of the compound of formula XIII with a stoichiometric excess of elemental zinc in a strong acid to deprotect the sulfur and form the compound of formula XIV

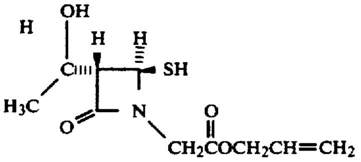

XIV (c) treatment of the compound of formula XIV with a hydroxy protecting group to form the compound of formula XIV(a)

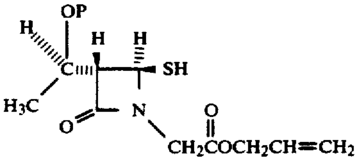

XIV(a)

wherein P is a hydroxy protecting group as hereinabove defined;

(d) reaction of the compound of formula XIV or XIV(a) with a thiocarbonyl compound of formula VII $$S{=}C(—Y)_2 \qquad VII$$

wherein Y is a leaving group to form a compound of formula XV

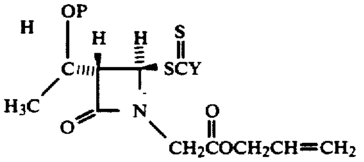

XV wherein Y and P are as hereinabove defined;

(e) treatment of compound XV with a non-nucleophilic strong base to form a compound of formula IX(a') which is tautomeric with formula IX(b')

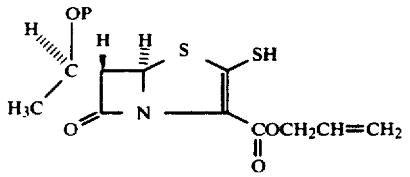

IX(a')

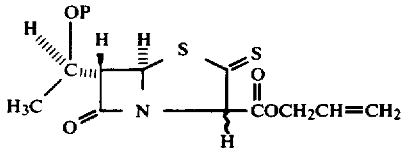

IX(b')

wherein P is as hereinabove defined;

(f) treatment of the compounds of formulas IX(a') and IX(b') under conditions which effect removal of the hydroxy protecting group when P is a hydroxy protecting group.

Unless otherwise stated, the term "loweralkyl" includes branched- and straight-chain alkyl groups of from 1 to 4 carbons and includes, for instance, methyl, ethyl, n-propyl, isopropyl, t-butyl and the like.

The term "fluoro loweralkyl" includes branched- and straight-chain loweralkyl groups substituted with 1 to 6 fluoro groups.

The term "organic radical" includes the groups lower alkyl; loweralkyl substituted with one or more substituents independently selected from halogen, hydroxy, lower alkoxy, cyano, oxo, carb(lower)alkoxy, carbamoyl, amino, lower alkyl amino, dilower alkyl amino, lower alkanoylamino, lower alkylthio, arylthio, heterocyclicthio,

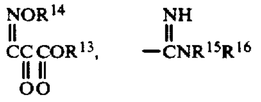

(wherein $R^{14}$ and $R^{13}$ are independently hydrogen or lower alkyl and $R^{15}$ and $R^{16}$ are each lower alkyl or $R^{15}$ and $R^{16}$ together with the nitrogen to which they are attached form a cyclicamino ring of 3 to 6 members) butanolidyl, aryl, heteroaryl or aryl or heteroaryl substituted with 1 to 4 substituents independently selected from lower alkyl, hydroxy, lower alkoxy, halogen, halo lower alkyl, lower alkylthio, amino, lower alkyl amino, dilower alkyl amino, carboxy lower alkyl, nitro, and cyano;

Aryl or aryl substituted with 1 to 4 substituents independently selected from lower alkyl, hydroxy, lower alkoxy halogen, halo lower alkyl, lower alkylthio, amino, lower alkyl amino, dilower alkyl amino, carboxy lower alkyl, nitro and cyano;

Heteroaryl or heteroaryl substituted with 1 to 4 substituents independently selected from lower alkyl, hydroxy lower alkoxy, halogen, halo lower alkyl, lower alkylthio, lower alkyl sulfonyl, amino, lower alkyl amino, dilower alkylamino, carboxy lower alkyl, nitro and cyano.

The term "halogen" means fluoro, chloro and bromo.

The term "loweralkanoylamino" means the group

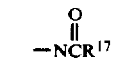

wherein $R^{17}$ is lower alkyl.

The term "aryl" means aromatic groups of 6 to 10 carbons and includes phenyl, napthyl and the like.

The term "heterocyclic" means cyclic groups of 5 or 6 ring atoms wherein 1 to 4 ring atoms are selected from the group consisting of nitrogen, sulfur and oxygen and includes for instance piperidyl, piperizinyl, pyrrolidinyl, thiazolidinyl, thiomorpholinyl, morpholinyl, tetrahdrofuranyl, tetrahydropyranyl, tetrahydrothiofuranyl, and tetrahydrothiopyranyl. Also included are the positional isomers of the above, e.g. 3-piperidinyl and 4-piperidinyl, 2-pyrrolidinyl and 3-pyrrolidinyl.

The term "heteroaryl" means aromatic heterocyclic groups of 5 to 10 ring atoms wherein 1 to 4 ring atoms are selected from the group consisting of nitrogen, sulfur and oxygen and includes for instance imidazoyl, pyridinyl, pyrimidinyl, thiazolyl, pyrrolyl, pyrazolyl, pyrazinyl, furyl, thiofuryl, triazolyl, oxazolyl, 1,2,3-oxadiazole, indolyl, benzothiofuranyl, tetrazolyl and the like.

The term "alkali metal" means sodium and potassium salts.

The term "removable hydroxy protecting group" means any such group conventionally used for this purpose, with the only requirement being compatability with the hydroxy substituent on the penems and removability utilizing elemental zinc or any other conventional agent for this purpose which will not adversely affect the penem structure. For the purpose of this invention, preferred hydroxy protecting groups include trichloroethoxycarbonyl, dimethyltributylsilyl, trimethylsilyloxycarbonyl and trimethylsilyl.

The preferred stereochemistry of the reactants and the intermediates in the above processes is as indicated in the various formulas, i.e. (5R,6S,8R). However, it is to be understood, that the process of this invention is operative for other stereoisomers and involves the selection of the starting material of the desired stereochemical configuration.

In a highly preferred embodiment of processes A and B of the present invention, the intermediates formed in each reaction step are not isolated but remain in the reaction vessel and are treated according to the next reaction step. This facilitates the process to a very great extent, since several steps can be carried out in the same solvent, without regard to separation of the desired product.

For instance, in a preferred embodiment of process A the mixed ester of formula III is added to the intermediate of formula II to form the hydroxy intermediate of formula IV. This intermediate of formula IV is then directly treated with the chlorinating agent, preferably thionyl chloride, to form the chloro intermediate of formula V. This intermediate, again without isolation, is treated directly with elemental zinc in a strong acid such as hydrochloric acid to concommitantly remove the hydroxy protecting group on the 6-substituent, the sulfur protecting group $R^1$ and the chlorine atom to afford the intermediate of formula VI. Thus steps (a), (b) and (c) of either of the aforementioned processes are conducted in the same reaction vessel, in the same solvent, and without any wastage caused by isolation of the intermediate compounds.

Again, in a preferred embodiment, the intermediate of formula VI or VI(a) are utilized directly in steps (e) and (f) without isolation. Thus, steps (d), (e) and (f) are conducted sequentially.

It is likewise preferred to dispense with the isolation of the intermediate of formulas IX(a) and IX(b) when preparing compounds of formula I. Thus steps (g), (h) and (i) may be conducted sequentially.

The first step (a) of processes A and B of this invention wherein an azetidinone of formula II is reacted with a compound of formulas III(a) and III(b) to form the intermediate of formula IV is typically conducted in a suitable organic solvent at about room temperature. Preferably, the organic solvent is a polar organic solvent, such as dimethylformamide, but other suitable solvents such as tetrahydrofuran, acetonitrile and dimethylsulfoxide may also be used. The compounds of formulas III(a) and III(b) are diesters, mixed esters or monoesters and their hydrated forms. They are represented by the following formulas III(a) and III(b)

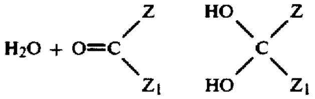

IIIa IIIb wherein Z and $Z_1$ are as defined above;

$R^2$ is trimethylsilyl, t-butyldiphenylsilyl or other equivalently functioning lower alkylsilyl group, cyano or a sulfone ester of the formula $—SO_2$ aryl. Preferred are the trimethylsilyl and t-butyldiphenylsilyl groups, with trimethylsilyl being most preferred due to its ready availability and ease of use.

Step (b) of these processes wherein the compound of formula IV is chlorinated to form the compound of formula V is typically conducted in a suitable organic solvent at temperatures of about −15° C. to 10° C. in the presence of an acid acceptor. Where the solvent utilized is also an acid acceptor, for instance, pyridine, no additional reagent is utilized. Alternatively, an organic solvent such as methylene chloride, chloroform, dimethyl formamide or acetonitrile may be utilized. In these cases, a separate acid acceptor, organic or inorganic must be added to the reaction mixture. Typical of the suitable acid acceptors are organic bases such as pyridine or triethylamine and inorganic bases such as sodium or potassium carbonate. As mentioned hereinabove, the chlorinating reaction may be carried out directly on the product of step (a) without isolation of the product. When this is the case, the solvent utilized is necessarily identical to that utilized in step (a). The chlorinating agent itself may be any of a variety utilized for the conversion of alcohols to chlorides such as thionyl chloride, oxalyl chloride, phosphorus oxychloride. Of these, thionyl chloride is most preferred.

Step (c) of these processes wherein the chlorinated intermediate of formula V is dechlorinated and the sulfur group and the hydroxy group of the 6-substituent concommitantly deprotected to form the intermediate of formula VI may likewise be conducted in the same solvent utilized for steps (a) and (b). However, any suitable organic solvent can be utilized, for instance, tetrahydrofuran, methylene chloride or dimethylformamide. Water, or any proton source, adjusted by the addition of a strong acid, is added to enhance the activity of zinc. Typical temperatures range from −15° C. to about room temperatures (about 25° C.) with a temperature of about 0° C. being particularly preferred. Most preferably, the removable hydroxy protecting and sulfur protecting groups utilized are those which are removable by elemental zinc. However, in the event that a removable hydroxy protecting group is utilized which is not so removable (by the zinc), a separate removal step is simply conducted to remove the hydroxy protecting group. This separate removal step may occur immediately after step (c) of the instant process, or at any other time after step (c) convenient to the conduct of the process. Such removal steps are well-known in the β-lactam art.

Step (d) of these processes involves the protection of the 6-hydroxy substituent. Optionally, if during step (c) the 6-hydroxy protecting group was not removed, this step may be eliminated. Hydroxy protecting group are well known in the beta-lactams art. A particularly preferred reagent for this step is bis silylacetamide which readily forms the trimethylsilyl protecting group at the 6-hydroxy moiety. Preferably step (d) is conducted directly upon the completion of step (c) without isolation of the intermediate of formula V. Thus the inert solvent utilized, e.g. DMF, may be the same as the one used in step (d). Solvents such as chloroform, methylene chloride and the like may also be employed in step (d). Temperatures for the reaction of step (d) range from 0° C. to 30° C.

Step (e) of the process is wherein the intermediate of formula VI or VI(a) is converted to the thiocarbonyl compound of formula VIII by reaction of the compound of formula VI or VI(a) with the thiocarbonyl reagent of formula VII. Typically, this step (e) is conducted directly upon the completion of step (d) without isolation of the intermediate of formula VI or VI(a). However, the intermediate of formula VI or VI(a) is sufficiently stable to be isolated and characterized. Thus, the solvent utilized may be the same as the one used in step (d). Temperatures for the reaction of step (e) range from about 10° C.–45° C., with room temperature (about 25° C.) being generally preferred. The thiocarbonyl reagent of formula VII has the following structure $$S{=}C(—Y)_2 \qquad VII$$

wherein Y is a leaving group. Typical of such leaving groups are chloro, bromo, iodo, imidazolyl or aryloxy such as naphthyloxy. For the purposes of the processes of this invention, 1,1'-thiocarbonyldiimidazole or beta-naphthyloxythiocarbonylchloride are preferred.

Step (f) of these processes involves the removal of the 6-hydroxy protecting group to form the compound of formula VIII(a). Methods for the removal of this group are well known in the β-lactam art. Preferably, when the 6-hydroxy protecting group is trimethylsilyl, addition of a mild aqueous acid solution, such as acetic acid, to the same solution as is employed on step (e) effects removal. Thus there is no need to isolate the compound of formula VIII before preceeding to step (f).

Step (g) of these processes involves the removal of the $Z_1$ protected carboxy group at position 3 of the compounds of formula VIII to afford the tautomeric compounds having formulas IX(a) and IX(b) which exist in equilibrium. The reaction of step (g) is typically conducted in a suitable organic solvent such as tetrahydrofuran, ethyl ether or dioxane at temperatures ranging from about 10° C.–45° C., with room temperature (about 25° C.) being preferred. One functional equivalent of fluoride ion is added so that only the $Z_1$ protected carboxy group, preferred by the trimethylsilylethyl protecting group, is removed. Typically, tetrabutylammonium fluoride is utilized as a source of fluoride ion, although any equivalent source of fluoride ion may be similarly utilized. When tetrabutylammonium fluoride is employed, a stoichiometric excess may be employed so long as only one functional equivalent is employed. Whereas tetrabutylammonium fluoride dissociates slowly in these solutions and as the removal of the Z protecting group, particularly when Z has an allyl protecting group is much slower than removal of the trimethylsilylethyl protected carboxy group, an excess (2 eq) of tetrabutylammonium fluoride results in only one functional equivalent being employed in this reaction step. Isolation of the product at this stage affords the compound of formulas IX(a) and IX(b) which may be utilized for further synthesis of penems.

Step (h) of this process involves the reaction of the compound of formulas IX(a) and IX(b) with a compound of the formula R-$Z^2$ wherein R is as hereinabove defined and $Z^2$ is a leaving group to form a compound of formula XI. Typically, this reaction step (f) is a continuation of step (f), and is conducted without isolation of the compound of formula IX(a) and IX(b). Thus, under such circumstances, the solvents utilized in steps (f) and (g) are necessarily the same. When a compound of formulas IX(a) and IX(b) is isolated, the solvents and temperatures suitable for step (g) can be different from those of step (f) but preferably are the same.

Alternatively, step (h) may be conducted by addition of fluoroloweralkyl trifluoromethyl sulfonate (i.e., 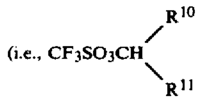

wherein $R^{10}$ and $R^{11}$ are as hereinabove defined) to IX(a) and IX(b). The reaction is typically conducted in a suitable organic solvent such as tetrahydrofuran and the like. An essentially equimolar amount of an acid acceptor, such as carbonate, is added to the system to facilitate the reaction. Typically, the reaction is conducted from about −5° C. to 30° C. and is generally complete from within 1 to 24 hours.

Step (i) of these processes involves the removal of the protecting group on the 3-carboxyl to form a compound of formula I. When the protecting group is allyl, removal is effected by the addition of a compound of formula XI to a solution containing palladium (zero) and an alkali alkyl carboxylate, or aqueous carbonate. This step is described by McCombie in U.S. Pat. No. 4,314,942 which is incorporated herein by reference. Most preferably, under these conditions, step (i) proceeds with the removal of the allyl protecting group and the formation of the alkali salt of the penem (Formula I) in situ. If the protecting group is $-CH_2CH_2-R_2$, the reaction conditions and reagents are identical to those used in step (e) of this process. Preferably tetrahydrofuran is used as the solvent, the temperature is room temperature (about 20°-25° C.) and tetrabutylammonium fluoride is the fluoride ion source.

Preferably, however, the compound of formulas IX(a) and IX(b) are prepared according to process C.

In a highly preferred embodiment of process C of the present invention, the intermediates formed in some of the reaction steps are not isolated but remain in the reaction vessel and are treated according to the next reaction step. This facilitates the process to a very great extent, since several steps can be carried out in the same solvent, without regard to separation of the desired product.

For instance, in the preferred embodiment of process C, the α-substituted allyl acetate of formula XII is added to the azetidione of formula II(a) to form the intermediate of formula XIII.

Again, in the preferred embodiment, the intermediate of formula XIII is utilized directly in steps (b) and (c) without isolation. Thus, steps (b) and (c) are conducted sequentially.

Likewise steps (d) and (e) are conducted sequentially without the necessity of isolating the intermediate.

Step (a) of process C involves the reaction of an azetidione of formula II(a) at 15°-30° C. in the presence of an acid acceptor with an α-substituted allyl acetate of formula XII $$WCH_2\overset{O}{\overset{\|}{C}}CH_2CH{=}CH_2 \qquad XII$$

wherein W is a leaving group, to form the compound of formula XIII. Preferred W leaving groups include tosyl, mesyl, chloro, bromo, iodo, and trifluoromethansulfonyl. Particularly preferred W leaving groups include iodide or bromide.

Where the solvent utilized is also an acid acceptor, for instance, pyridine, no additional reagent is utilized. Alternatively, an organic solvent such as acetonitrile may be employed. In these cases, a separate acid acceptor, organic or inorganic must be added to the system. Preferably, the reaction is conducted in acetonitrile employing cesium carbonate or tetra alkyl ammonium hydroxide as the acid acceptor.

Step (b) of this process involves the conversion of the compound of formula XIII to the corresponding thiol of formula XIV by deprotecting the sulfur with a stoichiometric amount of elemental zinc in hydrochloric acid under the same conditions as in step (c) of processes A and B above. Step (c) of this process involves the protection of the 6-hydroxy substituent to form the compound of formula XIV(a) with the preferred protecting group being trimethylsilyl whereas step (d) of the process is that wherein a compound of formula XIV or XIV(a) is converted to a compound of formula XV by addition of a thiocarbonyl reagent of formula VII which as the following structure $$S{=}C(-Y)_2 \qquad VII$$

wherein Y is a leaving group. Typical of such leaving groups are chloro, bromo, iodo, imidazolyl and aryloxy such as naphthyloxy. For the purposes of this process, 1,1'-thiocarbonyldiimidazole or beta-naphthyloxythiocarbonylchloride are preferred. Steps (b), (c) and (d) of process C are conducted as described for steps (e) and (f) of processes A and B described hereinabove.

Step (e) of this process involves the cyclization of the compound of formula XV into the thione of formulas IX(a') and IX(b'). The reaction is typically conducted in an anhydrous inert organic solvent such as tetrahydrofuran and the like. An essentially equimolar amount of a strong base such as lithium diisopropyl amide (LDA), lithium di-(trimethylsilyl)amine and the like is added to the system to effect cyclization. Typically, the reaction is conducted at from −50° to −100° C. and preferably at −70° C. and is generally complete from within 5 minutes to 24 hours.

Step (f) of this process involves the removal of the 6-hydroxy protecting group when P is a protecting group in the compound of formulas IX(a') and IX(b'). This step is accomplished as described hereinabove for step (f) of process A and B.

The following preparations, examples and illustrations describe in detail the processes of the present invention, methods for their preparation of the starting material and illustrations of the use of the intermediates produced by the instant process. Throughout these preparations, examples and illustrations, "NMR" denotes nuclear magnetic resonance spectra; "rotation" denotes optical rotation of the compounds in a suitable solvent; "MS" denotes mass spectra; UV denotes ultraviolet spectra; and "IR" denotes infrared spectra. Chromatography is preformed on silica gel unless otherwise noted. The term "room temperature" refers to about 18°-25° C. It will be apparent to those skilled in the art that many modifications, both of materials and methods, may be practiced without departing from the purpose and intent of this invention.

PREPARATION OF STARTING MATERIALS

EXAMPLE 1

Preparation of (3S,4R)-3-(1-trichloroethoxycarbonyloxyethyl)-4-triphenylmethylthioazetidin-2-one Add to a 250 ml flask 7.8 gm (0.0223 moles) of 3-(1-trichloroethoxycarbonyloxyethyl)-4-acetoxyazetidino-2-one, 220 ml acetonitrile, 2.6 gms (0.252 moles) cesium carbonate, and 5.2 gm (0.0188 moles) triphenylmethanethiol (tritylthiol). After stirring for 5 hours, an additional 1.0 gm (0.0036 moles) triphenylmethanethiol is added and the mixture is stirred for another one-half hour. After overnight regrigeration, the solids are removed by filtration and the solvents by evaporation under vacuum. The crude reaction product is chromatographed on coarse silica gel eluting with methylene chloride changing to 10% and 20% ethyl acetate/-methylene chloride to afford 7.89 grams (3S,4R)-3-(1-trichloroethoxycarbonyloxyethyl)-4-(triphenylmethylthio)azetidin-2-one with spectra as follows:

NMR: =7.7-7.1, 16H; 5.05, 1H, ; 4.85,2H, q(J=18 Hz); 4.45, 1H, d(J=1.5 Hz); 3.3, 1H, dd (J=1.5, 9 Hz); 1.5, 3H, d (J=6 Hz).

EXAMPLE 2

Preparation of Allyl-trimethylsilylethylketomalonate

Add to a 500 ml flask 25 gm ketomalomic acid 1½ $H_2O$, 250 mg p-toluene sulfonic acid, 58 gm allyl alcohol, and 200 ml benzene. Reflux with a Dean Stark tube for 6½ hours. Remove excess allyl alcohol and benzene by evaporation under vacuum. Wash the residue with $H_2O$, then distill at 2 mm Hg and collect dially ketomalonate as a yellow oil, b.p. 89°-92° C., yield 25 gm. Add 25 gm dially ketomalonate to 14.9 gm of $(CH_3)_3SiCH_2CH_2OH$, then add ½ ml of 1,5-diazabicyclo[4.3.0]non-5-ene (DBN). After 24 hours, wash the resultant mixture with cold 10% phosphoric acid, then with water. Dry the resultant product and distill at 0.4 mmHg to obtain allyl trimethylsilylethylketo malonate, b.p. 91°-100° C., yield 12 gm.

NMR: =0.05, (9H, S); 1.05, (2H, T, J=9 HZ); 4.35, (2H, T, 9 HZ); 4.70, (2H, D, J=6 Hz); 5.25, (2H, M); 5.80, (1H, M)

EXAMPLE 3

Di(trimethylsilyl)ketomalonate (a) In 100 ml of methylene chloride is dissolved 22.50 grams 2-trimethylsilylethanol. To this is added 20.00 grams triethylamine. After cooling to about −20° C., a solution of 15 grams of freshly distilled malonyl dichloride in 100 ml methylene chloride is added slowly over a period of one and one-half hours. After the addition is completed, the reaction mixture is allowed to warm to room temperature and then is washed twice with 500 ml portions of water, followed by washings with 5% sodium bicarbonate solution until the pH is greater than 9. The solution is then dried over anhydrous magnesium sulfate and the solvents removed by evaporation to yield 30.22 grams of the product, the trimethylsilyl diester of malonic acid.

(b) The diester prepared as described in paragraph (c) herein is dissolved in 300 ml benzene. To this solution is added 140 mg benzoic acid, 17 ml benzaldehyde and sufficient piperidine to afford a pH of about 9. The solution is refluxed with a Dean-Stark tube for 8 hours and then the solvents are removed under vacuum to afford, as the product, di(-trimethylsilylethyl)benzlidinemalonate.

(c) The benzylidene malonate prepared as described in paragraph (b) herein is dissolved in 500 ml methylene chloride and cooled to about 0° C. Ozone is then bubbled into the solution until a distinct blue to blue-green color persists. The ozone is then discontinued and the solution is allowed to stand for five to ten minutes. Nitrogen is then passed into the reaction vessel until the excess ozone is completely removed. 75 milliliters of dimethyl sulfide is added and the reaction mixture is allowed to come to room temperature. The solution is then evaporated to dryness and the resulting oil is placed in an open dish to allow any excess benzaldehyde to oxidize. After standing overnight, the semicrystalline mass is dissolved in methylene chloride and washed, first with saturated sodium bicarbonate solution, and then with water. The washed methylene chloride solution is dried over anhydrous magnesium sulfate and the solvents removed. The resulting oil/crystalline mass is recrystallized from petroleum ether to afford di(trimethylsilyl)ketomalonate.

EXAMPLE 4

Preparation of (5R,6S,8R)-allyl-2-thiol-6-(1-hydroxyethyl)penem-3-carboxylate (A) Preparation of (3S,4R)-1-[1-hydroxy-1-allyloxycarbonyl-1-trimethylsilylethoxycarbonylmethyl]-3-[1-(2,2,2-trichloroethoxycarbonyloxyethyl)]-4-triphenylmethylthio)azetidin-2-one Add 100 mg of (3S,4R)-3-[1-(2,2,2)trichloroethoxycarbonyloxyethyl]-4-(triphenylmethylthio)-azetidin-2-one (prepared as described in Example 1 above) and 0.2 ml of dimethylformamide to a dry vial. Add 45 mg of allyl trimethylsilylethylketomalonate (prepared as described in Example 2 above), 0.0014 ml of pyridine and 0.0014 ml of triethylamine to the system. After standing at room temperature for 50 minutes, remove the solvent by stripping to give the title product.

(B) Preparation of (3S,4R)-1-[1-allyloxycarbonyl-1-chloro-1-trimethylsilylethoxycarbonylmethyl]-3-[1,(2,2,2)-trichloroethoxycarbonyloxyethyl]-4-(triphenylmethylthio)-azetidin-2-one Add 4.26 gm of (3S,4R)-1-[1-hydroxy-1-alloxycarbonyl-1-trimethylsilylethoxycarbonylmethyl]-3-[1-(2,2,2-tri-chloroethoxycarbonyloxyethyl)]-4-triphenylmethylthio)azetidin-2-one to a solution of 10 ml of methylene chloride, 2 ml pyridine and 1 gm of calcium carbonate. Cool the system to 0°-5° C. by placing the system in an ice bath. After cooling, slowly add 1.5 ml of thionyl chloride. After 25 minutes, the reaction is complete. Wash the reaction mixture with sodium bicarbonate solution of pH less than 8 and remove the solvent by stripping. Chromatograph the residue on silica gel using methlene chloride as the eluant to afford 3.48 gm of the title compound.

(C) Preparation of (3S,4R)-1-[1-allyloxycarbonyl-1-trimethylsilylethoxycarbonylmethyl]-3-[1-hydroxyethyl)]4-sulfhydryl azetidin-2-one Dissolve 3.48 gm of (3S,4R)-1-[1-allyloxycarbonyl-1-chloro-1-trimethylsilylethoxycarbonylmethyl]-3-[1-(2,2,2)-trichloroethoxycarbonyloxyethyl]-4-(triphenylmethylthio)azetidin-2-one in 50 ml of tetrahydrofuran. To the system add 15 ml of water and 8 gm of zinc dust. Place the system in an ice bath and add hydrochloric acid in portions over 1 hours. Stir the solution at 0°-5° C. for an additional 2 hours an then add 4 ml of hydrochloric acid and portionwise, an additional 6 gms of zinc dust. Continue the reaction for an additional 1 hours, filter and remove the solvent by stripping. Dissolve the crude product in methylene chloride and wash the organic solution with water. Purify the crude product by column chromatography on silica gel using an eluant 1% ethylacetate (methylene chloride changing to 25% ethylacetate) to afford the 1.64 gm of title compound.

NMR: =0.05, (5, 9H); 1.05, (m, 2H); 1.15, (D, 3H, J=6); 2.2, (5, 1H); 3.38, (DD, 1H); 3.7, (m); 4.2, (m); 4.5, (m); 5.2, (m, 2H); 5.8, (m, 1H).

(D) Preparation of (3S,4R)-1-[1-trimethylsilyloxyethyl]-[1-allyloxycarbonyl-1-trimethylsilylethoxycarbonylmethyl]-4-sulfhydryl azetidin-2-one Dissolve the entire amount of (3S,4R)-3-(1-hydroxyethyl)-[1-allyloxycarbonyl-1-trimethylsilylethoxycarbonylmethyl]-4-sulfhydryl azetidin-2-one obtained from step (c) above in 10 ml of anhydrous methylene chloride. Add 0.783 ml (0.00316 moles) of bis trimethylsilyl acetamide to the system. Stir the system at room temperature for 15 minutes to yield the title compound.

(E) Preparation of (5R,6S,8R)-2-thiocarbonyl-3-allyloxycarbonyl-3-trimethylsilylethoxycarbonyl-6-(1-trimethylsilyloxyethyl)penam After the completion of step (D) and to the same solution, add 619 mg (0.00316 moles) of 90% thiocarbonyl diimidazole to the system. Stir the system at room temperature for 20 hours and then filter the solution. Remove the methylene chloride by stripping. Chromatograph the crude product on silica gel eluting with 30% cyclohexane/methylene chloride changing to methylene chloride to afford 704 mg of the title compound.

NMR:=6.2-5.6, m, 1H; 5.65, d (J=1.5 Hz), 1H; 5.5-5.1, (m), 2H; 4.7, d (J=5.5 Hz), 2H; 4.5-4.1, m, 3H; 3.62, d, d (J=1.5, 4 Hz), 1H; 1.28, d(J=6 Hz), 3H, 1.2-0.85, m, 2H; 0.2-0, m, 18H.

(F) Preparation of (5R,6S,8R)-2-thiocarbonyl-3-allyloxycarbonyl-3-trimethylsilylethoxycarbonyl-6-(1-hydroxyethyl)-penam To a 25 ml flask add 100 mg of (5R,6S,8R)-2-thiocarbonyl-3-allyloxycarbonyl-3-trimethylsilylethoxycarbonyl-6-(1-trimethylsilyloxyethyl)penam, 1 ml of tetrahydrofuran 0.05 ml of water and 0.05 ml of acetic acid. Stir the system at room temperature for 12 hours. Add ethyl acetate to the solution and wash the organic phase with sodium bicarbonate solution, water and then brine. Dry the organic phase over anhydrous sodium sulfate, filter and remove the solvent by stripping to give the title compound.

NMR: =6.15-5.6, m, 1H; 5.69, d(J-2 Hz), 1H; 5.55-5.12, m, 2H; 4.8-4.6, M, 2H; 4.5-4.0, m, 3H; 3.67, d, d(J=2, 7 Hz), 1H; 2.8-2.3, m, 1H; 1.37, d(J=6. Hz), 3H; 1.2-0.8, m, 2H; 0.3-0, m, 9H.

(G) Preparation of (5R,6S,8R)Allyl-2-thiol-6-(1-hydroxyethyl)penem-3-carboxylate To 7.7 mg of (5R,6S,8R)-2-thiocarbonyl-3-allyloxycarbonyl-3-trimethylsilylethoxycarbonyl-6-(1-hydroxyethyl)penam in 1 ml of tetrahydrofuran slowly add at room temperature 2 equivalents of tetrabutylammonium fluoride in 40 ml of tetrohydrofuran. Thin layer chromatography (silica gel, 10% ethylacetate/-methylene chloride) shows the immediate presence of the monodeprotected decarboxylated compound (5R,6S,8R)allyl-2-thiocarbonyl-6-(1-hydroxyethyl)penam-3-carboxylate.

NMR: =d 5.85, d (J=1 Hz), 1H; 5.8, m, 1H; 5.25, 5, 1H; 5.4-5.1, m, 2H; 4.7, 2H; 4.25, m, 1H; 3.65, d,d J=1, 1 Hz), 1H; 2.1, 1H; 1.35, d (J=7 Hz) 3H.

EXAMPLE 5

Preparation of Allyl (5R,6S,8R)-2-thiol-6-(1-hydroxyethyl)penem-3-carboxylate and Allyl (5R,6S,8R)-2-thiocarbonyl-6-(1-hydroxyethyl)penem-3-carboxylate (A) Preparation of (3S,4R)-1-(allyloxycarbonylmethyl)-3-(1-hydroxyethyl)-4-(triphenylmethylthio)azetidin-2-one Add 3 gm of (3S,4R)-3-(1-hydroxyethyl)-4-(triphenylmethylthio)azetidin-2-one to 10 ml of acetonitrile containing 0.286 gm of cesium carbonate. Add 0.2 gm of α-iodo allyl acetate to the system. Stir the sytem at room temperature for 16 hours. Dilute the ether (50 ml), filter and wash the ether layer with 1% aqueous phosphoric acid, followed by water. After drying over sodium sulfate remove solvent to give a foamy solid NMR: =8.4, 1H, s; 7.65, 1H, d(J=1 Hz); 7.05, 1H (dJ=1 Hz); 5.95, 1H, d (J-2 Hz); 5.8, 1H, m; 5.45-5.1, 2H, m; 4.3, 1H, m; 4.1, 2H, Q(J-16 Hz); 3.5, d,d (J=2,6); 1.35; 3H, d, (J=6 Hz).

(B) Preparation of (3S,4R)-3-(1-hydroxyethyl)-1-allyloxycarbonylmethyl-4-sulfhydryl-azetidin-2-one Add 500 mg of (3S,4R)-1-(allyloxycarbonylmethyl)-3-(1-hydroxyethyl)-4-(triphenylmethylthio)azetidin-2-one and 20 ml tetrahydrofuran to a 50 ml flask. Add zinc dust and 10% hydrochloric acid in small portions over 1 hour until all of the starting material is reacted. Recover the product by filtering off the excess zinc and removing the solvent to crystallize the title product.

NMR: $(CDCl_3)$=6.2-5.7(1H, m); 5.5-5.15 (2H, m); 5.0 (1H, dd, J=3,9 c/s); 4.75-4.55 (2H, m); 4.45-3.95 (1H, m); 4.14(1H, d, J=18 c/s); 3.78(1H, d, J=18 c/s);

3.19(1H, dd, J=6,3 c/s); 2.09(1H, d, J=9 c/s); 1.34 (3H, d, J=6 c/s).

(C) Preparation of (3S,4R)-3-(1-trimethylsilyloxy-ethyl-1-allyloxycarbonylmethyl-4-sulfhydryl-azetidin-2-one Add the entire amount of (3S,4R)-3-(1-hydroxyethyl)-1-allyloxycarbonylmethyl-4-sulfhydryl-azetidin-2-one produced in step (B) above to 25 ml of methylene chloride. To this system add 1.1 ml of bis silylacetamide. Stir the system at room temperature for 15 minutes to give the title compound.

(D) Preparation of (3S,4R)-1-(allyloxycarbonylmethyl)-3-(1-trimethylsilyloxyethyl)-4-(1'-imidazolylthiocarbonylthio)azetidin-2-one After completion of step (C) above and to the same solution add 350 mg of thiocarbonyldiimidazole. Stir the system at room temperature for 3 hours. Filter the solution and wash the precipitate with methylene chloride. Collect the filtrate and remove the methylene chloride by stripping. Chromatograph the residue on silica gel eluting with 20% ethyl acetate/methylene chloride to yield 335 mg of the title compound.

(E) Preparation of (5R,6S,8R)-allyl-2-thiol-6-(1-trimethylsilyloxyethyl)penem-3-carboxylate and (5R,6S,8R)-allyl-2-thiocarbonyl-6-(1-trimethylsilyloxyethyl)penam-3-carboxylate Add 170 mg of (3S,4R)-1-(allyloxycarbonylmethyl-3-(1-trimethylsilyloxyethyl)-4-(1'imidazolylthiocarbonylthio)azetidin-2-one to 40 ml of anhydrous tetrahydrofuran under a nitrogen atmosphere. Cool the system to −78° C. and then add 0.6 ml of 1M lithium di(trimethylsilyl)amine in hexane dropwise to the system. Stir the system at −78° C. for 5 minutes. Add 0.2 ml of acetic acid to the system. Dilute the system to 200 ml with methylene chloride. Wash the organic solution with water, aqueous sodium bicarbonate solution and again with water. Purify the product by chromatography by rapidly eluting the sample through silica gel with 5% ethyl acetate/methylene chloride to afford 125 mg of the desired products and the desilylated products.

(F) Preparation of (5R,6S,8R) Allyl-2-thiol-6-(1-hydroxyethyl)penem-3-carboxylate and (5R,6S,8R) Allyl-2-thiocarbonyl-6-(1-hydroxyethyl)penam-3-carboxylate To a 25 ml flask add the entire mixture produced in step (E) along with 5 ml of tetrahydrofuran, 1 ml of water and 1 ml of acetic acid. Stir the system at room temperature for 2 hours. Add ethyl acetate to the solution and wash the organic phase with sodium bicarbonate solution, water and then brine. Dry the organic phase over anhydrous sodium sulfate, filter and remove the solvent by stripping to give the title compound.

EXAMPLE 6

Preparation of (5R,6S,8R) Allyl-2-ethyl-thiol-6-(1-hydroxyethyl)penem-3-carboxylate To the solution of (5R,6S,8R) allyl-2-thiol-6-(1-hydroxyethyl)penem-3-carboxylate and (5R,6S,8R) allyl-2-thiocarbonyl-6-(1-hydroxyethyl)penam-3-carboxylate produced in step (F), Example 5 above add 0.016 ml of ethyl iodide and 16 mg sodium bicarbonate in 0.5 ml water. Stir the system at room temperature for 15 minutes. Add 25 ml of ethyl acetate to the system. Wash the organic solution with water, dry the organic phase with anhydrous sodium sulfate, filter and remove the solvent by stripping to yield the title compound.

EXAMPLE 7

Preparation of (5R,6S,8R) Allyl-2-(2',2',2')-trifluoroethyl)-6-(1-hydroxyethyl)-penem-3-carboxylate 1. Dissolve 0.735 ml pyridine in 25 ml dry toluene and cool to −20° C. under nitrogen. Add 1.45 ml trifluoromethanesulfonic anhydride followed by 0.703 ml 2,2,2-trifluoroethanol and allow to warm to room temperature. Wash the resultant residue with water, dry with anhydrous sodium sulfate and distill, collecting all fractions with a b.p. less than 100° to obtain trifluoromethyl 2,2,2-trifluoroethylsulfonate.

2. Add (5R,6S,8R) allyl-2-thiol-6-(1-hydroxyethyl)-penem-3-carboxylate and (5R,6S,8R) allyl-2-thiocarbonyl-6-(1-hydroxyethyl)penam-3-carboxylate (the product produced by the deprotection of 628 mg of (5R,6S,8R)-2-thiocarbonyl-3-allyloxycarbonyl-3-trimethylsilylethoxycarbonyl-6-(1-hdroxyethyl)penam with 2 equivalents of tetrabutylammonium fluoride) to 3 ml of tetrahydrofuran and 5 ml of trifluoromethyl 2,2,2-trifluoroethylsulfonate. Add 1 equivalent of potassium carbonate (powder) to the system. Continue the reaction at room temperature for 1½ hours and then store the solution in the refrigerator overnight. Remove the solution from the refrigerator and stir at room temperature for 1 hour. Filter the solution and wash with methylene chloride/2% phosphoric acid. Remove the solvent by evaporation. Dissolve the residue in warm 1:1 chloroform:petroleum ether and cool. The product crystallizes from solution to yield 168 mg of the title compound.

3. (5R,6S,8R)allyl-2-substituted thio-6-(1-hydroxyethyl)penem-3-carboxylates are readily coverted to their corresponding alkali salts by removal of the allyl protecting group as described by McCombie in U.S. Pat. No. 4,314,942, which is incorporated by reference herein. This removal is effected by the addition of the allyl ester to a solution containing palladium (zero) and an alkali alkylcarboxylate, carboxylic acid or aqueous carbonate.

DESCRIPTION OF THE PROCESS STEPS OF THIS INVENTION

EXAMPLE 8

(5R,6S,8R)-2-ethylthio-6-(1-hydroxyethyl)penem-3-carboxylic acid

A. 30.0 grams (3R,4R)-3-[1-(2,2,2)-trichloroethoxycarbonyloxyethyl]-4-(triphenylmethylthio)azetidin-2-one (prepared as described in Example 1) is dissolved in 6 ml dimethylformamide. To this solution is added 2.0 grams di(trimethylsilyl)ketomalonate (prepared as described in Example 3) and molecular sieves. After standing for two days at room temperature, the reaction mixture is partitioned between water and methylene chloride. The organic layer is separated and the solvents removed by a rotary evaporation. The crude reaction product is purified by column chromatography on silica gel eluting with methylene chloride changing to 2% ethyl acetate/methylene chloride to yield 4.26 grams (3R,4R)-1-[1-hydroxy-1,1-di(trimethylsilyloxycarbonyl)-methyl]-3-[1-(2,2,2)-trichlorethoxycarbonyloxyethyl]-4-triphenylmethlthio)azetidin-2-one, having spectra as follows:

NMR: =7.5-7.1,15H; 5.05,1H,m; 4.65,2H, s; 4.5,1H,d(J=1.5 Hz); 4.2,4H,m; 3.45,1H,dd(J=1.5,7 Hz); 1.05,3H,d.

B. To a solution of 10 ml methylene chloride, 2 ml pyridine and 1.0 gram calcium carbonate is added 4.26 gram (3R,4R)-1-[1-hydroxy-1,1-di(tri-methyl silyloxycarbonyl)methyl]-3-[1-(2,2,2-trichloroethoxyethoxycarbonyloxyethyl]-4-triphenylmethylthio)azetidin-2-one. After placing the mixture in an ice bath, 1.5 ml of thionyl chloride is slowly added. After one-half hour, the reaction is complete. The reaction mixture is then washed with sodium bicarbonate solution of pH less than 8 and the solvent removed under vacuum. Chromatography on silica gel using methylene chloride as eluant affords 3.48 grams of the product, (3R,4R)-1-[1-chloro-1,1-di(trimethylethoxycarbonyloxyethyl)methyl]-3-[1-(2,2,2)-trichloroethoxycarboxyloxyethyl]-4-(triphenylmethylthio)azetidin-2-one.

C. 3.48 grams of (3R,4R)-1-[1-chloro-1,1-di-(trimethylsilyloxycarbonyl)methyl]-3-[1-(2,2,2)-trichloroethoxycarbonyloxylthyl]-4-triphenylmethylthio)azetidin-2-one is dissolved in 50 ml tetrahydrofuran. To this solution is added 15 ml water and 8 grams zinc dust. The mixture is then placed in an ice bath and 16 grams of hydrochloric acid is added in portions over a period of one hour. After a period of two hours, 4 ml of 10% hydrochloric acid is added, and then, portionwise, an additional 6 grams of zinc dust. After a further period of one hour, the reaction mixture is filtered, and the solvents removed under vacuum. The crude product is partitioned between water and methylene chloride. Purification by column chromatography on silica gel using as eluant, 1% ethyl acetate/methylene chloride changing to 25% ethyl acetate/methylene chloride affords 1.644 grams of the desired product, (3R,4R)-1-[1,1-di(trimethylsilyloxycarbonyl)methyl]-3-(1-hydroxyethyl)-4-sulfhydrylazetidin-2-one, having spectra as follows:

D. (3R,4R)-3-(1-hydroxyethyl)-1-di(β-trimethylsilylethyl-2-malonate)]-4-sulfhydryl-azetidin-2-one- is dissolved in 2 ml methylene chloride and to this solution is added 68 mg (0.000346 moles)1,1'-thiocarbonyldiimidazole. After stirring another hour, an additional 60 mg of 1,1'-thiocarbonyldiimidazole is added. Stirring is continued for another 1.5 hour, at which time, the reaction mixture is applied directly to a chromatography column of silica gel. Elution with methylene chloride affords the desired product, (5R,6S,8R)-2-thiocarbonyl-3,3-di(trimethylsilyloxy-carbonyl)methyl-6-(1-hydroxyethyl)penam, having spectra as follows:

NMR: =5.7,1H,d(J=1 Hz); 4.2,5H,m; 3.65, 1H,dd(J=1,8 Hz); 1.3,3H,d(J=8 Hz); 0.95,4H,m; 0.05, 18H.

E. 61 milligrams of (5R,6S,8R)-2-thiocarbonyl-3,3-di(trimethylsilyloxycarbonyl)methyl-6-(1-hydroxyethyl)penam is dissolved in 5 ml tetrahydrofuran and 2 equivalents of tetrabutylammonium fluoride in 10 ml tetrahydrofuran is slowly added at room temperature. Thin layer chromatography (silica, 10% ethyl acetate/-methylene chloride) showed the immediate presence of the monodeprotected decarboxylated compound (5R,6S,8R)-2-thiocarbonyl-3-(trimethylsilyloxycarbonyl)methyl-6-(1-hydroxyethyl)penam, which exists in equilibrium with (5R,6S,8R)-2-thiol-3-(trimethylsilyloxycarbonyl)methyl-6-(1-hydroxyethyl)penem as follows F. To the solution of (5R,6S,8R)-2-thiocarbonyl-3-(trimethylsilyloxycarbonyl)methyl-6-(1-hydroxyethyl)penam and (5R,6S,8R)-2-thiol-3-(trimethylsilyloxycarbonyl)-methyl-6-(1-hydroxyethyl)penem produced in the above step E is added 2 ml of ethyl iodide. The reaction mixture is then partitioned between water and ethyl acetate. The organic layer is separated, and the solvents are removed by rotary evaporation to yield the desired product, (5R,6S,8R)-β-(trimethylsilyl)ethyl-2-ethylthio-6-(1-hydroxyethyl)penem-3-carboxylate, having spectra as follows:

NMR: =5.7,1H,d(J=1.5 Hz); 4.2,5H,m; 3.7,1H,dd(J=1.5,7 Hz); 3,2H,m; 1.4–0.9,8H; 0.05,9H.

G. 40 miligrams of (5R,6S,8R)-β-(trimethylsilyl)ethyl-2-ethylthio-6-(1-hydroxyethyl)penem-3-carboxylate is dissolved in 1 ml tetrahydrofuran and to this is slowly added one equivalent of tetrabutylammonium fluoride in 2 ml tetrahydrofuran at room temperature. After 15 minutes, the reaction is complete as shown by thin layer chromatography. Acidification with phosphoric acid to a pH not below 2, followed by purification affords the desired product, (5R,6S,8R)-2-ethylthio-6-(1-hydroxyethyl)penem-3-carboxylic acid, identifiable by spectra and bioautogram with authentic (5R,6S,8R)-2-ethylthio-6-(1-hydroxyethyl)penem-3-carboxylic acid.

EXAMPLE 9

Repetition of the procedures detailed in Example 8, steps A thru G, except substituting methyl iodide for the ethyl iodide utilized in step F, affords (5R,6S,8R)-2-methylthio-6-(1-hydroxyethyl)penem-3-carboxylic acid.

EXAMPLE 10

Substantial repetition of the procedures detailed in Example 8 utilizing n-propyliodide in place of the ethyl iodide of step F yields (5R,6S,8R)-2-n-propylthio-6-(1-hydroxyethyl)penem-3-carboxylic acid.

EXAMPLE 11

Using the identical materials except for the substitution of isopropyl iodide for the ethyl iodide of step F and repetition of the procedures detailed in Example 8 affords (5R,6S,8R)-2-isopropylthio-6-(1-hydroxyethyl)-penem-3-carboxylic acid.

EXAMPLE 12

Following the procedures detailed in Example 1 but utilizing ethylene and a radical initiator known in the art, such as AIBN[2,2'-azobis(2-methylpropionitrile)] in step g in place of the ethyl iodide, there is afforded (5R,6S,8R)-2-ethylthio-6-(1-hydroxyethyl)penem-3-carboxylic acid.

By following the procedures outlined in Examples 4–12 above the following compounds which represent the broad applicablity of the process E of this invention may be prepared:

| R | R | R |
|---|---|---|
| 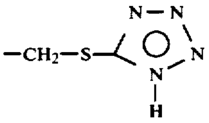 | 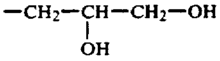 | 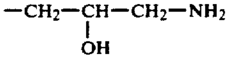 |
| 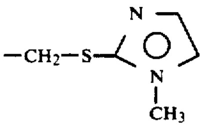 | 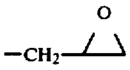 | 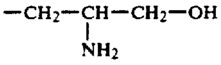 |
| 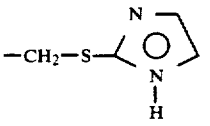 | 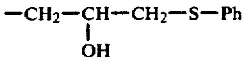<br>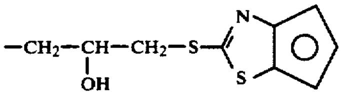 | 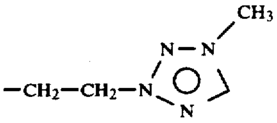<br>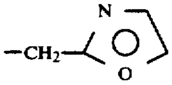 |
| 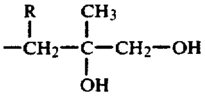 | 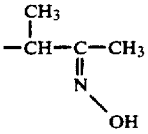 | 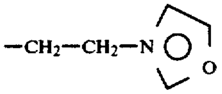 |
| 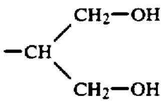 | 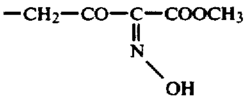 | 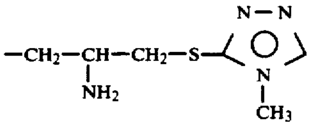 |
| 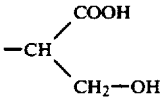 | 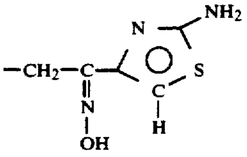 | 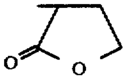<br>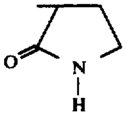 |
| 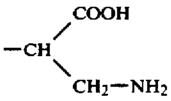<br>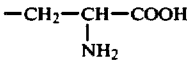 | $-CH_2-CH=N-OH$<br>$-CH_2-CH=N-O-CH_2-COOH$<br>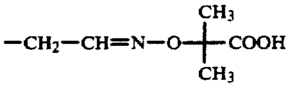 | 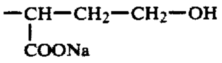 |
| 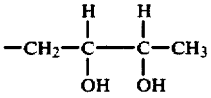 | 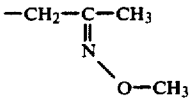 | 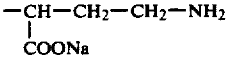 |
| 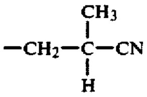 | $-CH_2-CH=N-OCH_3$ | 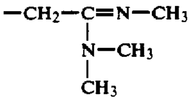 |
| 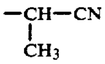<br>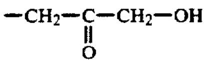 | 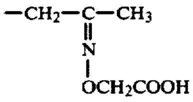 | 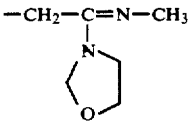 |

-continued
| R | R | R |
| --- | --- | --- |
| 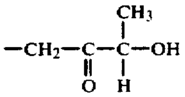 | 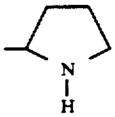 | 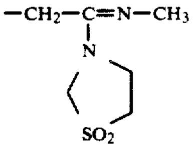 |
| 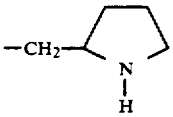 | 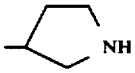 | 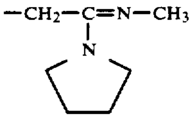 |
| 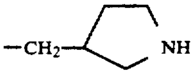 | 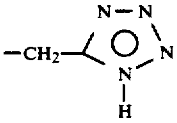 | 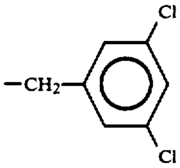 |
| 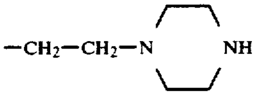 | 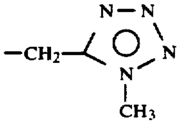 | 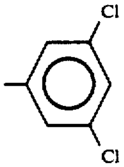 |
| 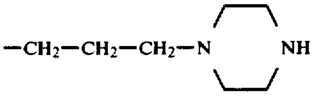 | | |
| 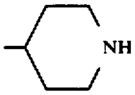 | 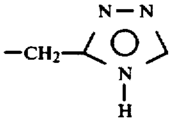 | 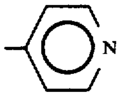 |
| 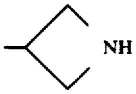 | 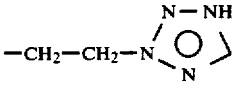 | 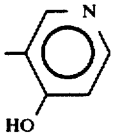 |
| | | 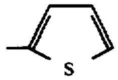 |
| 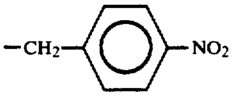 | 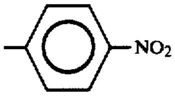 | |
| 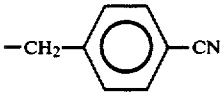 | 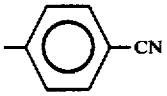 | |
| 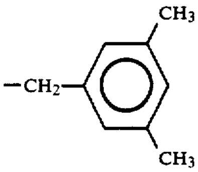 | 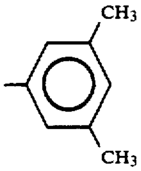 | 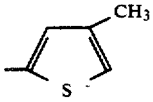 |

-continued
| R | R | R |
| --- | --- | --- |
| 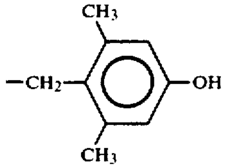 | 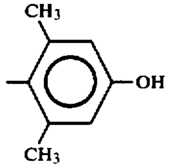 | 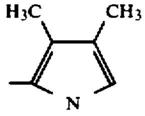 |
| 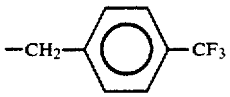 | 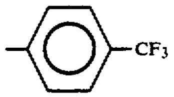 | 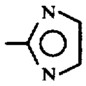 |
| 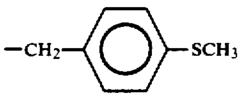 | 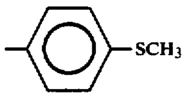 | 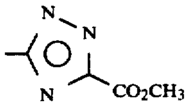 |
| 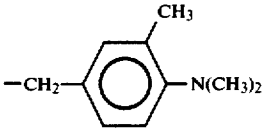 | 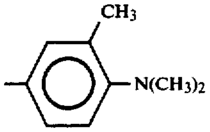 | 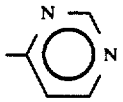 |
| 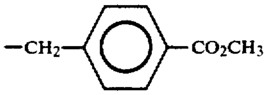 | 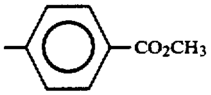 | 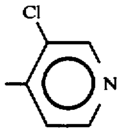 |
| 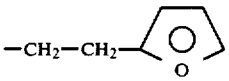 | 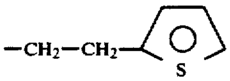 | 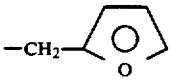 |
| 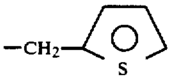 | 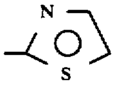 | 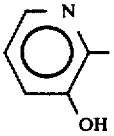 |
| 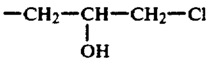 | 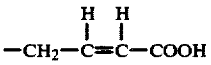 | 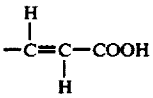 |
| 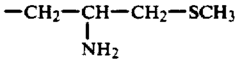 | 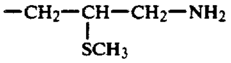 | 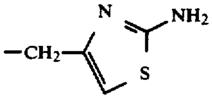 |
| 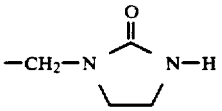 | 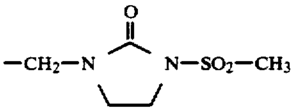 | |
We claim:
1. A process for the production of a compound of the formulas
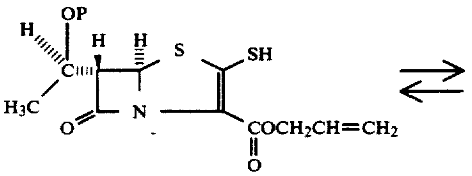
IX(a')

-continued

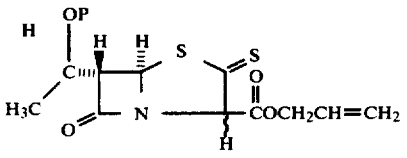

IX(b')

wherein P is a removable hydroxy protecting group or hydrogen; which comprises (a) reaction in the presence of an acid acceptor of an azetidinone of the formula II(a)

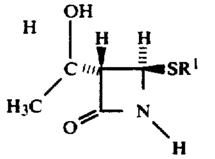

wherein $R^1$ is a sulfur protecting group selected from triphenylmethyl, dimethylphenyl, 2-pyranyl, or lower alkyl carbonyl; with an α-substituted allyl acetate of formula XII $WCH_2CO_2CH_2CH{=}CH_2$ XII wherein W is a leaving group selected from tosyl, mesyl, chloro, bromo, iodo or trifluoromethansulfonyl; to form the intermediate of the formula XIII

XIII

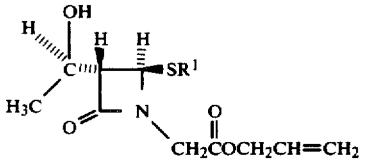

wherein $R^1$ is as hereinabove defined;

(b) treatment of the compound of formula XIII with a stoichiometric excess of elemental zinc in a strong acid to deprotect the sulfur and form the compound of formula XIV

XIV

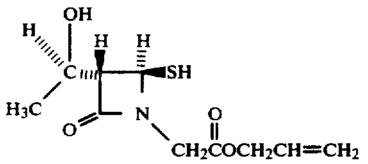

(c) treatment of the compound of formula XIV with a removable hydroxy protecting group to form the compound of formula XIV(a)

XIV(a)

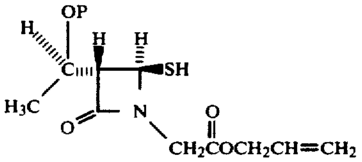

wherein P is a removable hydroxy protecting group;

(d) reaction of the compound of formula XIV or XIV(a) with a thiocarbonyl compound of formula VII $S{=}C(-Y)_2$ VII wherein Y is a leaving group selected from chloro, bromo, iodo, imidazolyl or aryloxy, to form a compound of formula XV

XV

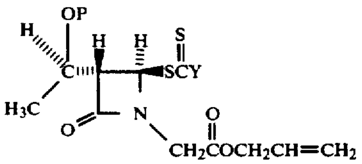

wherein Y is as hereinabove defined and P is a removable hydroxy protecting group or hydrogen;

(e) treatment of compound XV with a non-nucleophilic strong base to form a compound of formula IX(a') which is tautomeric with formula IX(b')

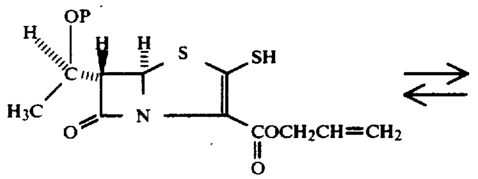

IX(a')

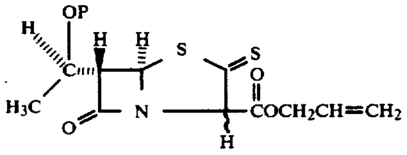

IX(b')

wherein P is a removable hydroxy protecting group or hydrogen.

* * * * *